United States Patent
Otsuka et al.

(10) Patent No.: US 9,287,099 B2
(45) Date of Patent: Mar. 15, 2016

(54) IONIZATION METHOD, MASS SPECTROMETRY METHOD, EXTRACTION METHOD, AND PURIFICATION METHOD

(71) Applicants: A SCHOOL CORPORATION KANSAI UNIVERSITY, Osaka (JP); CANON KABUSHIKI KAISHA, Tokyo (JP)

(72) Inventors: Yoichi Otsuka, Kawasaki (JP); Ryuichi Arakawa, Itami (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/973,305

(22) Filed: Aug. 22, 2013

(65) Prior Publication Data

US 2013/0341279 A1 Dec. 26, 2013

Related U.S. Application Data

(63) Continuation of application No. PCT/JP2013/001252, filed on Feb. 28, 2013.

(30) Foreign Application Priority Data

Mar. 1, 2012 (JP) ................................ 2012-045920

(51) Int. Cl.
*H01J 49/10* (2006.01)
*H01J 49/00* (2006.01)
*G01N 30/72* (2006.01)
*H01J 49/04* (2006.01)
*H01J 49/16* (2006.01)
(Continued)

(52) U.S. Cl.
CPC ............. *H01J 49/0027* (2013.01); *B01D 59/44* (2013.01); *G01N 30/7266* (2013.01); *H01J 27/08* (2013.01); *H01J 49/0454* (2013.01); *H01J 49/168* (2013.01)

(58) Field of Classification Search
None
See application file for complete search history.

(56) References Cited

U.S. PATENT DOCUMENTS

| 5,945,678 A | 8/1999 | Yanagisawa |
|---|---|---|
| 6,566,653 B1 | 5/2003 | Gerber |
| 6,627,882 B2 | 9/2003 | Schultz et al. |

(Continued)

FOREIGN PATENT DOCUMENTS

| CN | 101464427 A | 6/2009 |
|---|---|---|
| EP | 2 017 610 A1 | 1/2009 |

(Continued)

OTHER PUBLICATIONS

Patrick J. Roach et al., "Nanospray Desorption Electrospray Ionization: An Ambient Method for Liquid Extraction Surface Sampling in Mass Spectrometry" 135 Analyst 2233-2236 (2010).

(Continued)

*Primary Examiner* — Erik B Crawford
(74) *Attorney, Agent, or Firm* — Fitzpatrick, Cella, Harper & Scinto

(57) ABSTRACT

To achieve soft ionization more easily when a slight amount of substance is ionized under an atmosphere pressure. An ionization method for a substance contained in a liquid, including: supplying the liquid to a substrate from a probe and forming a liquid bridge made of the liquid containing the substance dissolved therein, between the probe and the substrate; oscillating the probe; and generating an electric field between an electrically conductive portion of the probe in contact with the liquid and an ion extraction electrode.

15 Claims, 6 Drawing Sheets

(51) Int. Cl.
*B01D 59/44* (2006.01)
*H01J 27/08* (2006.01)

(56) References Cited

U.S. PATENT DOCUMENTS

| | | | |
|---|---|---|---|
| 6,723,985 | B2 | 4/2004 | Schultz et al. |
| 6,737,640 | B2 | 5/2004 | Kato |
| 2013/0334030 | A1 | 12/2013 | Otsuka et al. |

FOREIGN PATENT DOCUMENTS

| | | | |
|---|---|---|---|
| JP | 9-306417 | A | 11/1997 |
| JP | 10-112279 | A | 4/1998 |
| JP | 2003-519889 | A | 6/2003 |
| WO | 01/50499 | A1 | 7/2001 |
| WO | 03/065405 | A1 | 8/2003 |

OTHER PUBLICATIONS

Kenzo Hiraoka, "Fundamentals of Mass Spectrometry: Fundamentals of Electrospray," 58(4) J. Mass Spectrom. Soc. Jpn. 139-154 (2010).

Dong Weon Lee et al., "Switchable Cantilever for a Time-of-Flight Scanning Force Microscope," 84(9) Appl. Phys. Lett. 1558-1560 (Mar. 2004).

International Search Report in PCT/JP2013/001252 (mailed May 14, 2013).

International Preliminary Report on Patentability in PCT/JP2013/001252 (issued Sep. 2, 2014).

Extended European Search Report in European Application No. 13754423.5 (dated Sep. 9, 2015).

Notification of Reason for Refusal in Japanese Application No. 2012-045920 (dispatched Nov. 10, 2015).

First Office Action in Chinese Application No. 201380020208.3 (notified Dec. 23, 2015).

MASS SPECTRUM OF MOUSE PANCREAS SECTION

IONIZATION METHOD, MASS SPECTROMETRY METHOD, EXTRACTION METHOD, AND PURIFICATION METHOD

CROSS-REFERENCE TO RELATED APPLICATIONS

This application is a continuation of International Application No. PCT/JP2013/001252, filed Feb. 28, 2013, which claims the benefit of Japanese Patent Application No. 2012-045920, filed Mar. 1, 2012.

BACKGROUND OF THE INVENTION

1. Field of the Invention

The present invention relates to an ionization method for a substance and a mass spectrometry method using the ionization method. The present invention also relates to an extraction method and purification method for a substance.

2. Description of the Related Art

A mass spectrometry method that is one of component analysis methods is a technique which involves ionizing components in a sample and measuring the mass-to-charge ratio (mass number/charge number) thereof.

In recent years, techniques of creating an image of the distribution of components existing on a solid sample surface are developed. For example, the distribution of a particular component is visualized as a mass image, whereby conditions of a sample can be determined. As an example of such techniques, a method of showing data that serves as the basis for a pathological diagnosis, based on a mass image of a pathological specimen including cancer tissue is developed. A mass image is generally acquired by: ionizing a sample at a plurality of measurement points on a sample surface; obtaining the mass-to-charge ratio of the generated ions for each measurement point; and associating a position on the sample surface with ion information. Hence, in order to improve the spatial resolution of the obtained mass image, a technique of ionizing a micro region on the sample surface is required.

For such a technique of ionizing components in a micro region on a sample surface, U.S. Pat. No. 6,566,653 and Dong Weon Lee et al., "Switchable cantilever for a time-of-flight scanning force microscope" Applied Physics Letters, 84, 1558 (2004) each propose a method of ionizing components on a solid substance surface using a cantilever-type probe configured to oscillate. According to this method, the probe has one pointed leading end and another end fixed to a cantilever, and the probe is driven such that the pointed leading end thereof reciprocates between a sample and the front of an ion take-in port of a mass spectrometer. The pointed leading end of the probe comes into contact with a micro region of the sample, so that components of the sample are attached to the pointed leading end of the probe. Then, voltage and laser light are applied to the pointed leading end of the probe in front of the ion take-in port, whereby only the components in the micro region that are attached to the pointed leading end of the probe can be ionized.

Further, Patrick J. Roach et al., "Nanospray desorption electrospray ionization: an ambient method for liquid extraction surface sampling in mass spectrometry" Analyst, 135, pp 2233-2236 (2010) proposes a method of: imparting a solvent to a micro region on a solid sample surface; dissolving components existing in the micro region; and ionizing the dissolved components under an atmosphere pressure. This method uses: a first capillary configured to supply the solvent for dissolving the components in the solid sample, to the sample surface; and a second capillary configured to move a mixture solution in which the components are dissolved in the solvent, to an ionization site. In the state where the two capillaries are close to the solid sample surface, the solvent is supplied thereto by the first capillary, whereby a liquid bridge is formed between the leading ends of the two capillaries and the sample surface. In the liquid bridge, only a contact portion of the solid sample is dissolved, and the dissolved portion is then introduced to the second capillary. A high voltage is applied to the solvent, and ionization is performed at the leading end of the second capillary. This method enables the ionization of the micro region. Further, because the ionization is performed under an atmosphere pressure, the time required for processing can be shortened, and the size of an apparatus can be reduced. Hence, this method is advantageous particularly when a large number of samples are analyzed.

In mass spectrometry for materials of biological origin such as biological tissue, in the case where molecules are non-selectively cut and fragmented during ionization thereof, it becomes difficult to identify components, and hence soft ionization, in which ionization is achieved without breaking biological components, is also required.

SUMMARY OF THE INVENTION

In the method disclosed in each of U.S. Pat. No. 6,566,653 and Dong Weon Lee et al., "Switchable cantilever for a time-of-flight scanning force microscope" Applied Physics Letters, 84, 1558 (2004), the components to be measured are one of atoms and molecules formed of a small number of atoms. This method has a problem that, when macromolecules of lipid, sugar, and protein are ionized, it is difficult to attach the macromolecules to the pointed leading end of the probe while maintaining the structure of the macromolecules and to achieve escape and soft ionization (ionization without cutting the molecular structure) thereafter.

It is difficult for the method disclosed in Patrick J. Roach et al., "Nanospray desorption electrospray ionization: an ambient method for liquid extraction surface sampling in mass spectrometry" Analyst, 135, pp 2233-2236 (2010), to form a liquid bridge having a size smaller than the closest distance of the leading ends of the two capillaries, and hence this method has a problem that improvement in spatial resolution achieved by making the ionization site smaller is difficult. Further, this method has another problem that a mechanism for precisely aligning the two capillaries and bringing the capillaries closer is required, the number of parts forming an apparatus increases, and the apparatus itself is more complicated.

An ionization method of the present invention is an ionization method for a substance contained in a liquid, including: (i) supplying the liquid onto a substrate from a probe and forming a liquid bridge made of the liquid containing the substance, between the probe and the substrate; and (ii) generating an electric field between an electrically conductive portion of the probe in contact with the liquid and an ion extraction electrode.

According to the present invention, when a slight amount of substance is ionized under an atmosphere pressure, improvement in spatial resolution can be achieved more easily.

DESCRIPTION OF THE EMBODIMENTS

Figure 1:
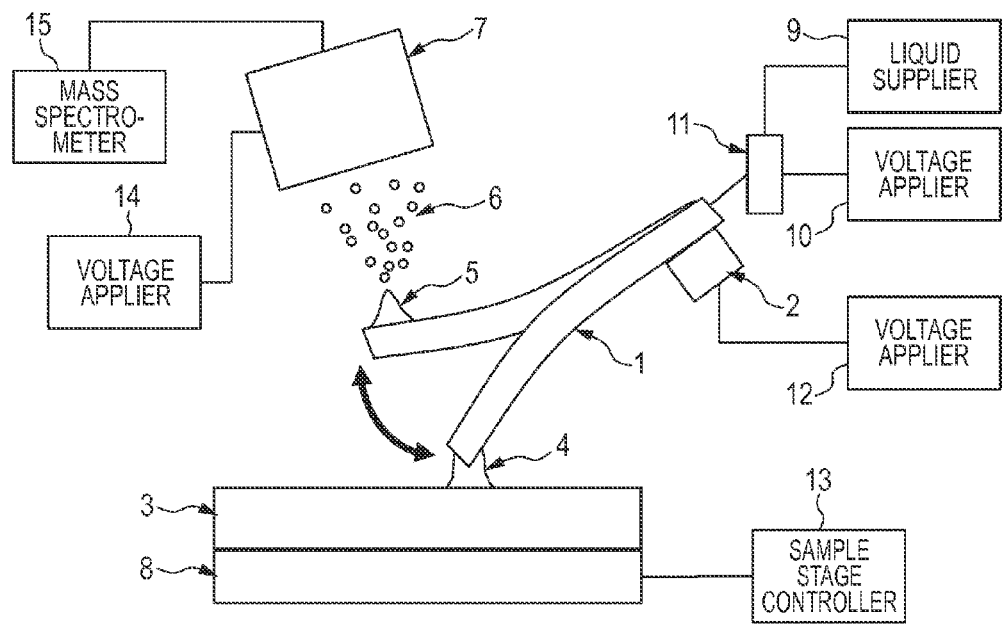
FIG. 1 is a diagram for describing a first embodiment of the present invention.

Hereinafter, a method of the present invention is described with reference to the drawings. An exemplary embodiment for carrying out the present invention is illustrated in FIG. 1. FIG. 1 illustrates: a probe 1 including a flow path through which a liquid passes; an oscillation provider 2 configured to oscillate the probe 1; a substrate 3; a liquid bridge 4 formed between the probe 1 and the substrate 3; a Taylor cone 5; charged micro droplets 6; an ion take-in part 7 including an ion extraction electrode for taking ions into a mass spectrometer; and a sample stage 8 configured to support the substrate. FIG. 1 also illustrates: a liquid supplier 9 configured to supply the liquid to the probe 1; a voltage applier 10; an electrically conductive flow path 11; a voltage applier 12; a sample stage controller 13; a voltage applier 14; and the mass spectrometer 15.

In the present invention, the liquid supplied from the liquid supplier 9 forms the liquid bridge 4 between the substrate 3 and the probe 1. Then, the liquid forming the liquid bridge 4 is changed to the charged micro droplets 6 by oscillations of the probe 1 and an electric field made by the voltage applier 10 and the voltage applier 14, whereby a measurement target component can be taken as ions into the ion take-in part 7.

That is, in the present embodiment, the probe corresponds to an imparting unit of the liquid onto the substrate, an acquiring unit of a substance, a transporting unit of the liquid to an appropriate position for ionization, and a forming unit of the Taylor cone for ionization.

The liquid supplier 9 supplies one of: a solvent for dissolving an analysis target element contained in a sample fixed onto the substrate 3; and a mixture solution of the analysis target element and a solvent for dissolving the analysis target element (hereinafter, the solvent and the mixture solution are collectively simply referred to as liquid). The liquid supplied from the liquid supplier 9 is guided to the flow path inside of the probe 1 via the electrically conductive flow path 11. At this time, voltage is applied to the liquid by the voltage applier 10 through the electrically conductive flow path 11. Any of DC voltage, AC voltage, pulse voltage, and zero voltage is applied to the liquid.

In the case where the entirety or a part of the electrically conductive flow path 11 is subsumed in the flow path inside of the probe 1 or piping for connection, the term "probe" in the present embodiment refers to a collective concept thereof. Further, even in the case where the electrically conductive flow path 11 is not subsumed in the flow path inside of the probe 1 or the piping for connection, the term "probe" in the present embodiment refers to a collective concept thereof in a broad sense. That is, at least part of the material forming the probe may be electrically conductive. Examples of the electrically conductive material include metal and semiconductor, and any material can be adopted therefor as long as the material shows a reproducible constant voltage value when voltage is applied thereto from the voltage applier. That is, in the present embodiment, voltage is applied to an electrically conductive portion of the probe, whereby voltage is applied to the liquid.

The phrase "applying voltage to the probe" in the present embodiment refers to: imparting an electric potential different from an electric potential of the ion extraction electrode to be described later, to the electrically conductive portion forming at least part of the probe; and generating an electric field between the electrically conductive portion forming at least part of the probe and the ion extraction electrode to be described later. As long as this electric field is achieved, the voltage applied here may be zero voltage. The material of the flow path 11 may be an electrically conductive substance, and examples of the material used therefor include stainless steel, gold, and platinum.

Examples of the used piping for connection of the probe 1, the electrically conductive flow path 11, and the liquid supplier 9 include capillaries configured to supply a slight volume of liquid, such as a silica capillary and a metal capillary, and the electrical conductivity thereof may be any of insulative, conductive, and semiconductive properties. Note that the electrically conductive flow path 11 may constitute part of a flow path in which the liquid supplied from the liquid supplier 9 passes through the inside of the probe 1 to be introduced to the leading end of the probe 1 opposite to the liquid supplier 9, and the position of the electrically conductive flow path 11 is not particularly limited. For example, the entirety or a part of the electrically conductive flow path 11 may be subsumed in the flow path inside of the probe 1 or the piping for connection. For such a configuration, it is possible to use a probe formed by inserting an electrically conductive material such as a stainless steel wire, a tungsten wire, and a platinum wire into a silica capillary.

In the case where the probe 1 itself is electrically conductive, the voltage applied to the electrically conductive flow path 11 is propagated to the probe 1, and voltage is applied to the liquid flowing through the flow path inside of the probe 1. The detail of such an embodiment is described later in a second embodiment of the present invention. Meanwhile, in the case where the probe 1 is insulative, the voltage applied to the electrically conductive flow path 11 cannot be propagated to the probe 1, but voltage is applied to the liquid flowing through the flow path 11, and this liquid is introduced to the probe 1. Consequently, even in the case where voltage is not propagated to the probe 1, voltage is applied to the liquid, so that the liquid is charged.

The liquid supplied from the liquid supplier 9 is provided onto the substrate 3 from the leading end of the probe 1. At this time, the sample may be fixed in advance onto the substrate, and a particular component as the analysis target element contained in the sample on the substrate 3 may be dissolved in the solvent provided by the probe 1. Alternatively, the mixture solution in which the analysis target element is mixed in advance with the solvent may be provided onto the substrate 3.

As a result, a slight amount of substance can be ionized with high resolution under an atmosphere pressure.

In the present embodiment, further, the probe 1 oscillates in the above-mentioned configuration. The expression "the probe 1 oscillates" in the present invention refers to that the probe 1 is driven such that the position of the leading end of the probe 1 on the substrate 3 side is spatially displaced. In particular, the probe can be curved and oscillated in a direction that intersects with the axial direction of the probe. The probe 1 can be oscillated by giving mechanical oscillations thereto from the oscillation provider 2. Alternatively, spontaneous resonance of the probe 1 may be used without the aid of the oscillation supplier 2.

It is generally known that the primary-mode intrinsic oscillation frequency of a cantilever-type object can be expressed by the cantilever arm length, the density, the cross-sectional area, the Young's modulus, and the second moment of area. Because the probe in the present embodiment is similar to such a cantilever-type probe, the intrinsic oscillation frequency of the probe can be controlled by adjusting the material of the probe, the probe size, the type and volume of the liquid supplied to the probe, and the magnitude of the electric field generated between the probe and the ion take-in part. In examples to be described later, silica is used as the material of the probe, but other materials may be used for the probe. For example, silicon, polymeric materials, and metal materials can be used for the probe, and materials having different densities and Young's moduli may be used for the probe. The oscillation supplier 2 may be an object that generates oscillations. For example, a piezoelectric element and an oscillation motor can be used for the oscillation supplier 2. The oscillations of the probe 1 may be any of continuous oscillations and intermittent oscillations, and the oscillation frequency thereof may be any of a resonant frequency and a non-resonant frequency. The timing of applying voltage to the liquid and the timing of supplying oscillations to the probe 1 can be determined as desired.

The frequency and amplitude of the oscillations of the probe 1 can be set to desired values, and may be held at constant values or modulated. For example, the frequency of the oscillations thereof can be adjusted as desired by changing a voltage value or a current value output from the voltage applier 12 electrically connected to the oscillation provider 2. Further, it is desirable to set the magnitude of the amplitude thereof such that the formation of a liquid bridge and the occurrence of ionization are both achieved and to change the settings as appropriate when the type of the probe and the magnitude of the electric field are changed.

For the oscillation direction of the probe 1, for example, two independent oscillation providers 2 are brought into contact with the probe 1, and oscillations in directions orthogonal to each other are generated, whereby curving oscillations in a desired direction can be given to the probe 1. Example types of such oscillations include uniaxial oscillations, a rotational motion, and a spiral motion. In the uniaxial oscillations, the probe oscillates in a uniaxial direction at a particular frequency and amplitude. For example, oscillations of a cantilever-type probe correspond to the uniaxial oscillations, and the oscillations can be approximated by a sine wave. In the rotational motion, biaxial oscillations orthogonal to each other are given to the probe, whereby the probe oscillates at a particular frequency and amplitude. At this time, the oscillations can be approximated by a synthesis of two sine waves, and this is known as a Lissajous figure.

If the probe 1 is sandwiched by a plurality of opposed oscillation providers 2, oscillations can be stably given to the probe 1.

In the present embodiment, because the probe 1 oscillates, it is possible to separately cause the state where the probe 1 and the substrate 3 are connected to each other with the intermediation of the liquid and the state where the probe 1 and the substrate 3 are separated from each other. The state where two objects are connected to each other with the intermediation of a liquid is generally referred to as liquid bridge. In the present embodiment, the liquid bridge 4 refers to the state where the liquid supplied from the probe 1 is in physical contact with at least both the probe 1 and the substrate 3.

That is, in the present embodiment, because one end of the probe is oscillated, alternately performed and achieved are: (i) supplying the liquid onto the substrate from the probe and forming the liquid bridge made of the liquid containing the substance, between the probe and the substrate; and (ii) generating the electric field for generating ions, between the electrically conductive portion of the probe in contact with the liquid and the ion extraction electrode.

Because the position of one end of the probe is changed by oscillations, an appropriate placement relation for performing the (i) supplying and forming and the (ii) generating can be set.

Because the liquid is continuously or intermittently supplied from the probe 1, the liquid bridge 4 is formed. When the liquid bridge 4 is formed, the probe 1 may be in contact with the substrate 3, and may not be in contact therewith. In the case where the probe 1 is in contact with the substrate 3, the liquid bridge 4 can be more stably formed.

In the state where the probe 1 is separated from the substrate 3 by oscillations, the liquid forming the liquid bridge 4 approaches the ion take-in part 7 including the ion extraction electrode electrically connected to the voltage applier 14. On this occasion, the liquid moves toward the side surface of the probe 1 on the ion take-in part 7 side, due to the electric field between: the electric potential of the liquid itself to which voltage is applied through the electrically conductive flow path 11; and the electric potential of the ion extraction electrode to which voltage is applied by the voltage applier 14, so that the liquid forms the Taylor cone 5. The side surface here refers to a portion in which electrospray is generated. In FIG. 1, the Taylor cone 5 is formed on a continuous surface forming the longer axis direction of the probe, but this position is influenced by the electric field between the ion take-in part 7 and the liquid and the wettability of the probe 1 with the liquid. Hence, the Taylor cone 5 may be formed at a position including other surfaces.

The electric field becomes larger at the leading end of the Taylor cone 5, electrospray is generated from the mixture solution, and the charged micro droplets 6 are generated. If the magnitude of the electric field is appropriately set, a Rayleigh fission occurs in the charged droplets, and ions of a particular component can be generated. The charged droplets and the ions are guided toward the ion take-in part 7 by a flow of air and the electric field. At this time, the oscillations of the probe can include a motion in a direction toward the ion take-in part 7 such that the electric field around the solution forming the Taylor cone is large. The Rayleigh fission here refers to a phenomenon in which the charged droplets 6 reach a Rayleigh limit and excessive electric charges in the charged droplets are emitted as secondary droplets. It is known that components contained in charged droplets are generated as gas-phase ions during the formation of a Taylor cone by a liquid, the generation of electrospray containing the charged droplets from the leading end of the Taylor cone, and the occurrence of such a Rayleigh fission. It is also known that a threshold voltage Vc at which electrospray is generated is $Vc=0.863(\gamma d/\epsilon_0)^{0.5}$ ($\gamma$: the surface tension of the liquid, d: the distance between the liquid and the ion extraction electrode, rc: the radius of an opening part of the flow path inside of the probe, and $\epsilon_0$: the permittivity in vacuum). (J. Mass Spectrom. Soc. Jpn. Vol. 58, 139-154, 2010)

The ion take-in part 7 is heated to a particular temperature between room temperature and several hundreds of degrees, and voltage is applied to the ion take-in part 7. At this time, it is necessary to adjust the voltage that is applied to the liquid by the voltage applier 10 and the voltage that is applied to the ion extraction electrode by the voltage applier 14 such that an appropriate electric field is generated so as to generate ions. Examples of the voltage applied by the voltage applier 14 include DC voltage, AC voltage, pulse voltage, zero voltage, and desired combinations thereof. Note that the electric field for generating ions is defined by the electric potential applied to the electrically conductive flow path 11 corresponding to the electrically conductive portion of the probe, the electric potential of the ion take-in part 7, and the distance between the liquid and the ion take-in part 7. Hence, depending on the types of a substance to be ionized and a solvent, these electric potentials and distance need to be set such that an appropriate electric field is generated.

After that, the ions are introduced to a mass spectrometer 15 connected to the ion take-in part 7, through a differential pumping system, and the mass-to-charge ratio of the ions is measured in the mass spectrometer 15. Desired mass spectrometers such as a quadrupole mass spectrometer, a time-of-flight mass spectrometer, a magnetic field deflecting mass spectrometer, an ion-trap mass spectrometer, and an ion-cyclotron mass spectrometer can be used as the mass spectrometer 15. Further, if the correlation between the mass-to-charge ratio (mass number/charge number; hereinafter, referred to as m/z) of the ions and the amount of generated ions is measured, the mass spectrum can also be obtained.

The size of the Taylor cone 5 changes depending on the flow rate of the liquid, the composition of the liquid, the shape of the leading end of the probe 1, the oscillation frequency of the probe 1, and the magnitude of the electric field. In the case where the Taylor cone 5 is extremely small, the form thereof may not be observable by a microscope, but there is no problem as long as ions are stably generated.

In the present embodiment, because the probe configured to oscillate is used, the timing at which the liquid bridge 4 is formed by the liquid and the timing at which electrospray is generated at the leading end of the Taylor cone and the substance is ionized are separated from each other. In other words, the formation of the liquid bridge 4 and the ionization of the substance occur at different timings.

For a temporal change in the generation of electrospray, the state where electrospray is generated and the state where the generation of electrospray is stopped alternately occur, and the cycle thereof is known to be about several hundreds of milliseconds. The reason for this is as follows: it is necessary to supply electric charges at an excessive density into a liquid, in order to cause the charged liquid to form a Taylor cone and thus generate electrospray; these excessive electric charges are emitted from the Taylor cone once the electrospray is generated; and electric charges need to be supplied until electrospray is generated again. (J. Mass Spectrom. Soc. Jpn. Vol. 58, 139-154, 2010)

In the present embodiment, because the probe configured to oscillate is used, the timing at which the liquid bridge is formed and the timing at which the solution containing a measurement target component dissolved therein generates electrospray can be controlled so as to be separated from each other. Consequently, the control of the timing and number of times of electrospray generation, which is difficult for conventional methods, can be facilitated. As a result, when a mass image to be described later is acquired, the number of times of electrospray generation at a position of a sample to be ionized can be kept constant, and the comparison of ion intensities on the mass image can be facilitated. It is difficult for conventional electrospray methods to accurately control the timing of charged droplet generation and the timing of electrospray stop, whereas the method of the present invention enables the control of these timings through appropriate oscillations of the probe.

Moreover, in the present embodiment, electrospray is not generated at the timing of liquid bridge formation. That is, at this timing, electric charges are supplied to the liquid, and the electric charges are suppressed from being emitted from the liquid. With this configuration, at the timing of electrospray generation, sufficient electric charges are accumulated in the liquid, and the electrospray can be efficiently generated. Moreover, in the present embodiment, in the state where electrospray is generated, a large electric field is applied to the liquid at the leading end of the probe, and an action of causing the charged droplets to be attracted toward the ion take-in part is produced. In addition, because the oscillation direction of the probe is adjusted to the ion attraction direction, the oscillation energy of the probe is imparted to the liquid forming the electrospray, the electric charge density at the leading end of the Taylor cone is increased, and an effect of promoting electrospray generation is produced.

Moreover, in the present embodiment, in the case where the probe configured to oscillate scans a sample surface, the period during which the solid sample surface and the probe interact with each other is shorter, and hence an effect of suppressing damage to the significantly rough solid sample surface can be produced. In the case where a probe configured not to oscillate scans a significantly rough solid sample, the probe may scrape the sample surface, and the surface shape may be changed.

According to the present embodiment, the formation time of the liquid bridge 4 is adjusted by controlling the flow rate of the liquid and the oscillation amplitude and oscillation frequency of the probe 1, whereby the volume of the liquid forming the liquid bridge 4 can be easily controlled. Hence, when the mixture solution in which the analysis target element is mixed in advance with the solvent is provided from the probe, the amount of the analysis target element to be ionized can be finely adjusted. Similarly, when the sample is fixed onto the substrate 3 and is dissolved in the solvent supplied from the probe, the size of a region with which the liquid bridge 4 comes into contact can be controlled by adjusting the formation time of the liquid bridge 4, and only components in the region having a desired size can be ionized.

In the case where the sample is fixed onto the substrate to be ionized, the position of the substrate stage 8 is changed by the sample stage controller 13, whereby the coordinates at an ionization target position of the sample can be controlled. Further, The coordinates of the ionization target position and the obtained mass spectrum are associated with each other, whereby the two-dimensional distribution of the mass spectrum can be obtained. Data obtained according to this method is three-dimensional data containing the coordinates (an X coordinate and a Y coordinate) of the ionization target position and the mass spectrum. After the ionization and the mass spectrum acquisition are performed at different positions, the amount of ions having a desired mass-to-charge ratio is selected, and the distribution thereof is displayed. Consequently, a mass image can be obtained for each component, and the distribution of a particular component on the sample surface can be captured. The sample may be moved such that the liquid bridge 4 formed by the probe 1 scans a desired plane to be measured.

Figure 2:
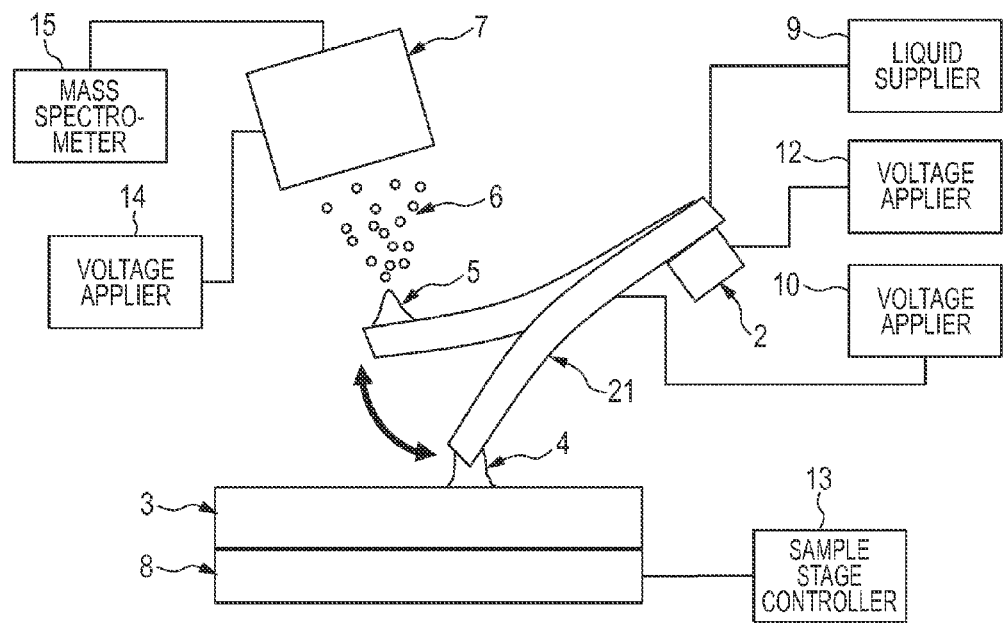
FIG. 2 is a diagram for describing a second embodiment of the present invention.

In the second embodiment of the present invention, as illustrated in FIG. 2, voltage may be applied to the liquid with the intermediation of a probe 21 including a flow path through which the liquid passes. At this time, a probe 21 is electrically connected to the voltage applier 10, and voltage is applied to the liquid supplied from the liquid supplier 9, with the intermediation of the probe 21. Note that, similarly to the above-mentioned embodiment, the phrase "applying voltage to the probe" refers to: imparting an electric potential different from an electric potential of the ion extraction electrode, to the electrically conductive portion forming at least part of the probe; and generating an electric field that enables ion generation between the ion extraction electrode and the probe. As long as this electric field is achieved, the voltage applied here to the electrically conductive portion forming at least part of the probe may be zero voltage. The material of the probe 21 may be an electrically conductive substance, and examples of the material used therefor include: metal such as stainless steel, gold, and platinum; and derivatives such as glass partially coated with metal.

Figure 3:
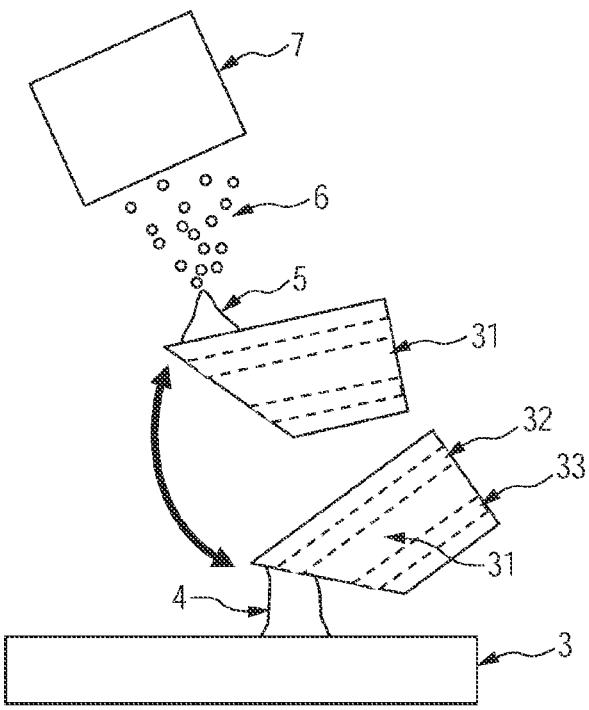
FIG. 3 is a diagram for describing a third embodiment of the present invention.

In a third embodiment of the present invention, as illustrated in FIG. 3, a probe 31 that can supply a plurality of types of liquid may be used. In FIG. 3, a probe 31 includes a first flow path 32 configured to supply a liquid and a second flow path 33 configured to supply a liquid. The liquid bridge 4 is formed between the first flow path 32 and the substrate 3. In comparison, the amplitude of oscillations and the angle of the probe are adjusted such that the leading end of the second flow path 33 does not come into contact with the sample, whereby the liquid that comes out of the second flow path 33 avoids forming a liquid bridge. Note that, at this time, different electric potentials can be independently given to the first liquid flowing through the flow path 32 and the second liquid flowing through the flow path 33, through electrically conductive flow paths different from each other.

Different types of liquid may be caused to flow through the first flow path 32 and the second flow path 33, or the same type of liquid may be caused to flow therethrough. For example, in the case of using different types of liquid, a solvent for dissolving components on the sample surface is introduced to the first flow path 32, and a solvent containing molecular species that react with a particular component included in the first liquid is introduced to the second flow path 33, whereby the particular component can be selectively ionized.

Meanwhile, in the case of using the same liquid, for example, the liquid that comes into contact with the sample surface to form a liquid bridge is introduced to both of the first flow path 32 and the second flow path 33. At this time, because the side surface of the probe 31 is always washed by the liquid that comes out of the second flow path 33, contamination of the side surface of the leading end of the probe can be prevented, and a decrease in spatial resolution of a mass image can be prevented.

The configuration described above is given as a mere example. Hence, a spatial position relation of the flow paths may be different, and a probe including three or more types of flow paths may be used.

Figure 4A:
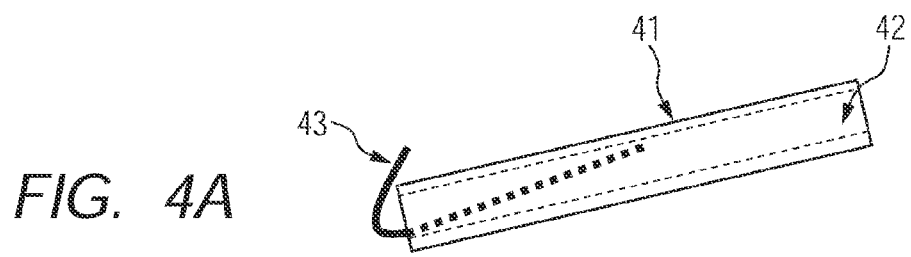
FIG. 4A is a diagram for describing a fourth embodiment of the present invention.
Figure 4B:
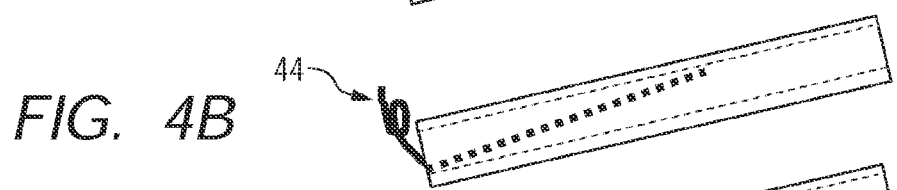
FIG. 4B is a diagram for describing a fourth embodiment of the present invention.
Figure 4C:
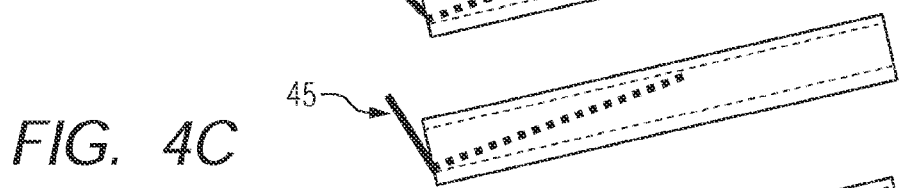
FIG. 4C is a diagram for describing the fourth embodiment of the present invention.
Figure 4D:
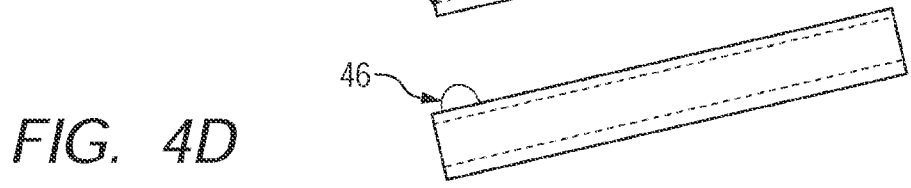
FIG. 4D is a diagram for describing the fourth embodiment of the present invention.

In a fourth embodiment of the present invention, as illustrated in FIGS. 4A, 4B, 4C, and 4D, if a protrusion made of a metal wire or the like is formed in the vicinity of the leading end of a probe, the formation of a Taylor cone and ionization can be stabilized. In each of FIGS. 4A, 4B, 4C, and 4D, a flow path 42 for causing a liquid to pass therethrough is formed in a probe 41. At this time, a metal wire 43 is inserted into the probe 41 so as to be partially exposed at the leading end of the probe 41. In order to form such a structure, for example, a metal wire made of platinum is inserted into the flow path 42, the platinum wire is exposed at the leading end of the probe 41, and the exposed end of the platinum wire is bent toward the ion take-in part 7 (FIG. 4A). Another end of the platinum wire is processed so as to be in contact with an inner wall portion of the flow path 42 and not to easily come off the probe 41. According to this method, the liquid forming a liquid bridge between the probe 41 and the substrate 3 spontaneously moves along the metal wire portion of the probe 41, and hence a Taylor cone is stably formed in the protrusion portion. If such a micro protrusion is formed, the charged liquid can be held at the leading end of the probe 41, and stable ionization can be achieved. The protrusion does not necessarily has such a shape as the metal wire 43, and a metal wire 44 (FIG. 4B) bent as desired and a linear metal wire 45 (FIG. 4C) can also be used. Substances other than the metal wires can also be used. For example, a protrusion 46 (FIG. 4D) may be formed by disposing a polymeric material such as an epoxy-based resin at the leading end of the probe.

In the present embodiments, an ionization target sample is not particularly limited. If the ionization target is an organic compound made of macromolecules of lipid, sugar, and protein, these substances can be easily soft-ionized according to the methods of the present embodiments.

Because each ion has an intrinsic mass-to-charge ratio, if the electric field around the ion is adjusted, only a particular ion can be separated. That is, a particular component in a mixture can be extracted and purified.

An example method of separating only a particular component includes: introducing a plurality of ion species into a vacuum chamber; separating ions using an electric field; and then collecting only particular ion components on a substrate in the vacuum chamber. With the use of this method, the substrate on which the ion components have been collected can be taken out of the vacuum chamber, and the ion components can be separated from the substrate using an appropriate solvent. Also, an object such as an artificial organ can be installed in a vacuum chamber, thereby imparting separated ions directly to the object. Example methods of generating an electric field include using a quadrupole electrode and using an ion-trap electrode.

According to the method of the present invention, for example, only a substance such as protein having an affinity for a particular site of a biological body can be separated from among a plurality of components contained in a fractured extract of a cultured cell. Then, if the separated particular component is imparted to the surface of a substance, functions of the particular component can be added to the substance. Further, if a component that specifically reacts with a particular disease site is imparted to the surface of a medicinal agent, an effect of improving medicinal benefits can be expected. Further, if a substance such as protein that is separated and purified according to the method of the present invention is imparted to the surface of an object such as an artificial organ that is used in a biological body, an effect of suppressing a rejection in the biological body can be expected.

EXAMPLES

Hereinafter, examples of an evaluation method according to the present invention are described in detail with reference to the drawings.

Example 1

Observation Using High-speed Camera of Ionization Method

Figure 5A:
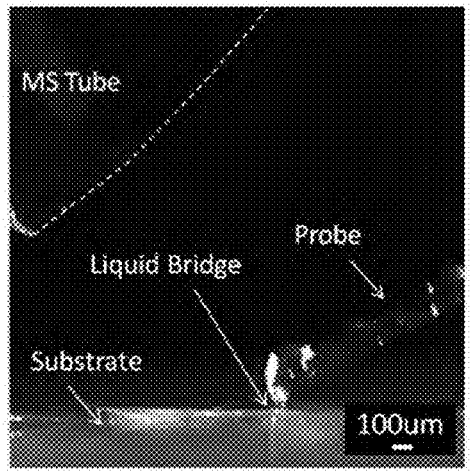
FIG. 5A is a picture illustrating a result of observing, using a high-speed camera, the state where a liquid bridge is formed and the state where ions are generated, according to Example 1.
Figure 5B:
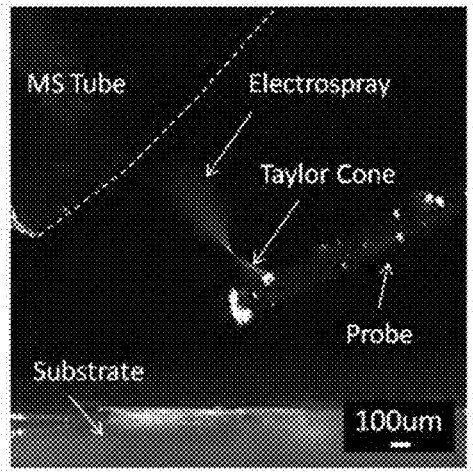
FIG. 5B is a picture illustrating a result of observing, using the high-speed camera, the state where a liquid bridge is formed and the state where ions are generated, according to Example 1.

FIGS. 5A and 5B show results of observing, using a high-speed camera, the state where a liquid bridge is formed and the state where ions are generated, using the method of the present invention. FIGS. 5A and 5B each illustrate the ion take-in part (MS Tube) including the ion extraction electrode for taking ions into the probe, the substrate, and the mass spectrometer illustrated in FIG. 1. TSQ7000 (Thermo Fisher Scientific K.K.), which was a quadrupole mass spectrometer, was used as the mass spectrometer. A silica capillary capable of supplying a liquid from the leading end thereof to the substrate was used as the probe, the silica capillary was connected to a metal needle of a syringe, and voltage was applied to the silica capillary by a voltage applier connected to the metal needle. The syringe was fixed to a syringe pump, and the liquid could be sent out at a constant flow rate from the syringe to the leading end of the probe. Glass was used for the substrate, and a mixture of water, methanol, and formic acid (water:methanol:formic acid=498:498:2) was used as the mixture solution. A voltage of 3 to 6 kV was applied to the probe. The flow rate of the solvent was 0.15 microliters/minute. The angle defined by the substrate and the probe was about 20 degrees, and the angle defined by the longer axis of a metal pipe (ion take-in part) and the substrate was about 40 degrees. MS Tube was connected to TSQ7000, an electric potential of 37.5 V was applied to the connection portion, and the temperature was set to 300° C. When the probe was oscillated in a spontaneous resonance mode, the state where the probe was closest to the substrate as illustrated in FIG. 5A and the state where the probe was farthest from the substrate and close to MS Tube as illustrated in FIG. 5B were alternately observed.

In the state of FIG. 5A, the formation of a liquid bridge was observed between the probe and the substrate. In comparison, in the state of FIG. 5B, the liquid bridge disappeared, the formation of a Taylor cone was observed in a portion of the probe, and misty droplets were observed at the leading end of the Taylor cone. The misty droplets were electrospray, and the micro droplets charged by the electric field were escaping from the leading end of the Taylor cone. From this result, it is considered that: the charged liquid flowed out of the leading end of the probe; the liquid moved toward a side wall portion of the leading end of the probe, under an influence of the spatial electric field around the liquid; the liquid formed the Taylor cone; and the liquid became the micro droplets to be attracted toward MS Tube. The spatial electric field around the Taylor cone is mainly influenced by the electric potential provided to the probe, the electric potential of MS Tube, and the distance between MS Tube and the charged liquid. In addition, in the state where the oscillating probe temporarily stops in the vicinity of MS Tube and where the velocity thereof becomes zero, the acceleration of the probe becomes highest. In this state, a largest force is applied to the charged liquid attached to the probe in a direction toward MS Tube, the direction being orthogonal to the longer axis of the probe, and this mechanical action is considered to produce an effect of promoting the formation of a Taylor cone and the generation of micro droplets.

In the state of FIG. 5A, when the probe was in contact with the substrate and the velocity of the probe was 0, the shape of the charged liquid in the side wall portion of the leading end of the probe deformed, and a Taylor cone was not formed. This is considered to be because force is applied to the liquid in a direction toward the substrate, the direction being orthogonal to the longer axis of the probe, and the formation of a Taylor cone is thus suppressed.

When the state of FIG. 5A and the state of FIG. 5B alternately occurred, mass spectrometry was performed on ions taken in from MS Tube, with the result that ions deriving from components in the mixture solution were detected. This shows that charged micro droplets were emitted from the leading end of the Taylor cone and that components inside of the droplets were ionized. As proved in this way, if the probe configured to oscillate is used, the timing of liquid bridge formation and the timing of Taylor cone formation can be separated from each other, and ionization can be stabilized by the Taylor cone.

Next, as a result of observing oscillations using the high-speed camera, the frequency of the oscillations was about 200 Hz, and the displacement amount of the probe between the formation position of the liquid bridge and the formation position of the electrospray was estimated to be about 500 micrometers. Moreover, it was confirmed that, in the case where the probe was lengthened, the frequency of the oscillations decreased. In the above example, the spontaneous resonance of the probe was used, but the oscillations of the probe were similarly observed also in the case where an oscillator was brought into contact with part of the probe. In this way, the oscillations can be controlled by changing the length of the probe. Otherwise, it is considered that the oscillations can be controlled by changing each parameter. It is generally known that the primary-mode intrinsic oscillation frequency of a cantilever-type object can be expressed by the cantilever arm length, the density, the cross-sectional area, the Young's modulus, and the second moment of area. Because the probe in the present embodiment is similar to such a cantilever-type probe, it is considered that the oscillations of the probe can be controlled by adjusting the material of the probe, the probe size, the type and volume of the liquid supplied to the probe, and the magnitude of the electric field generated between the probe and MS Tube.

Further, a protrusion was formed in the vicinity of the leading end of the probe, whereby the formation of a Taylor cone and ionization could be stabilized. A metal wire made of platinum or the like was inserted into the capillary so as to be exposed at the leading end of the capillary, and the platinum wire was protruded toward MS Tube. Then, an experiment similar to the above was carried out. As a result, the following state was confirmed: the charged liquid that flowed out of the leading end of the capillary formed a liquid bridge, the liquid then spontaneously moved along the platinum wire portion, and a Taylor cone was stably formed.

Example 2

Mass Spectrum Acquisition of Mouse Pancreas Section and One-dimensional Mapping (Mass-to-Charge Ratio: 50 to 1,000)

Figure 6:
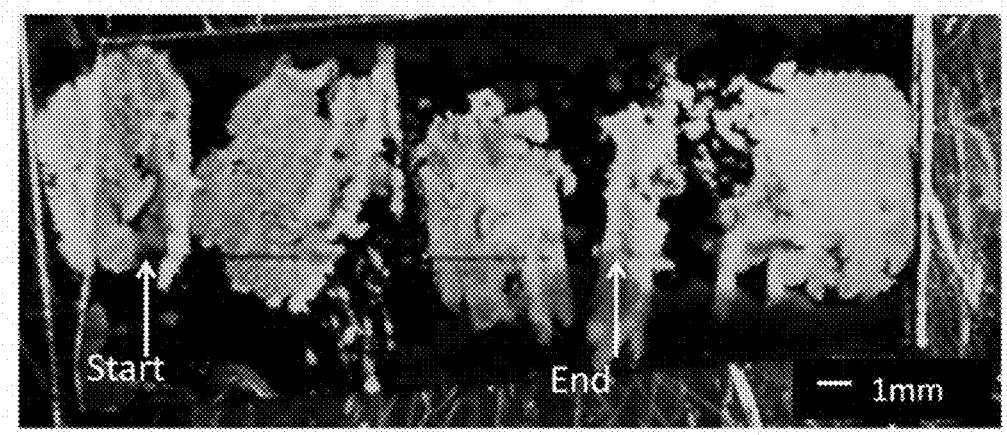
FIG. 6 is a picture illustrating the form of a sample used in Example 2.

Described are results of ionizing biological components according to the method of the present invention. The sample was prepared by slicing mouse pancreas tissue at a thickness of about 10 micrometers using a cryomicrotome and fixing the sliced sections onto a glass substrate. FIG. 6 illustrates the form of the sample ionized according to the method of the present invention. Portions brighter in contrast correspond to the pancreas tissue sections, and the number of the sections exiting on the glass substrate is five. A portion of the sample was ionized according to the method of the present invention, the portion existing on a line segment obtained by connecting two points indicated by arrows in FIG. 6 with a straight line. In the present example, the probe was configured to oscillate, and the intermittent formation of a liquid bridge was observed between the sample surface and the leading end of the probe. The sample was set so as to move in a uniaxial direction by 0.05 millimeters every two seconds. A quadrupole mass spectrometer (TSQ7000; Thermo Fisher Scientific K.K.) was used as the mass spectrometer. The mass-to-charge ratio for measurement was set to 50 to 1,000. The other experiment conditions were the same as the contents described in Example 1.

Figure 7:
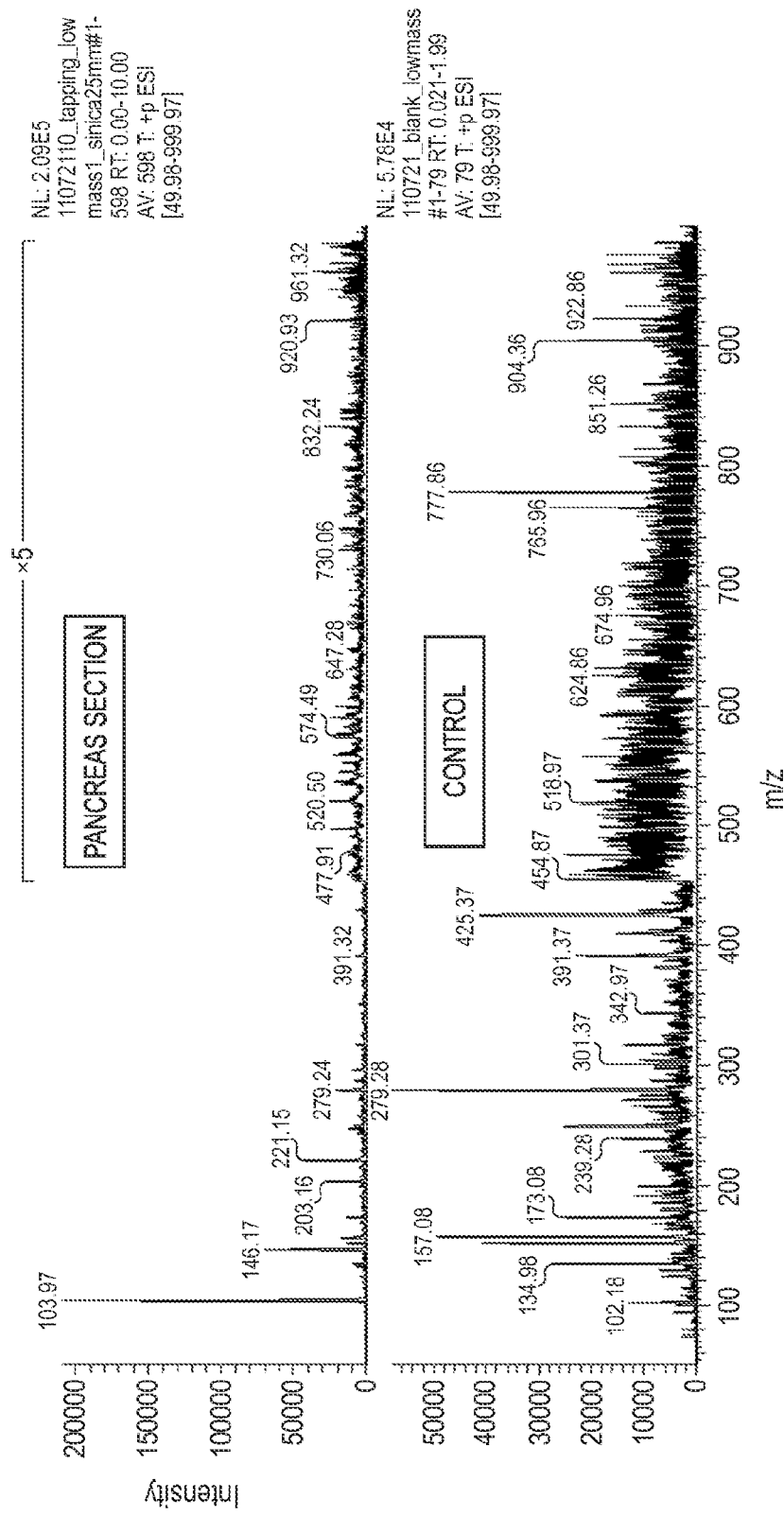
FIG. 7 illustrates mass spectra at a mass-to-charge ratio of 50 to 1,000, which are obtained in Example 2.

FIG. 7 illustrates the mass spectra obtained by the measurement. The spectrum comparison between the pancreas tissue and only the glass substrate (control) showed that ions specific to the pancreas tissue were detected. Table 1 shows the list of representative ion species of the pancreas tissue. Among the ion species, for example, m/z=103.97, 146.17 is considered to correspond to the mass of choline, acetylcholine contained in cells, and the signal of m/z=500 to 800 is considered to derive from lipid components. Meanwhile, almost no m/z corresponding to fragments thereof was detected. As proved in this way, components of biological tissue can be soft-ionized under an atmosphere pressure according to the method of the present invention.

TABLE 1

| m/z |
| --- |
| 103.9729 |
| 146.1654 |
| 156.06 |
| 203.1553 |
| 221.1521 |
| 243.1482 |
| 247.2475 |
| 258.0456 |
| 287.2404 |
| 296.1388 |
| 317.0351 |
| 351.229 |
| 365.4265 |
| 429.12 |
| 443.4127 |
| 496.6032 |
| 520.5 |
| 534.32 |
| 544.2948 |
| 552.2933 |
| 558.39 |
| 560.39 |
| 574.4894 |
| 576.79 |
| 582.388 |
| 598.53 |
| 606.48 |
| 614.38 |
| 630.3 |
| 734.67 |
| 758.6567 |
| 782.6525 |
| 796.52 |
| 812.53 |

Figure 8A:
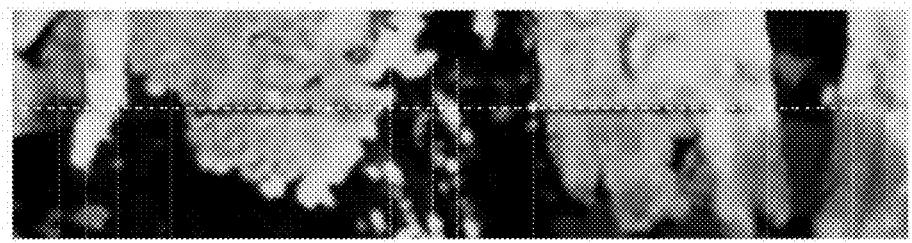
FIG. 8A is a picture illustrating a temporal change in ion intensity when a probe scans a tissue section, according to Example 2.
Figure 8B:
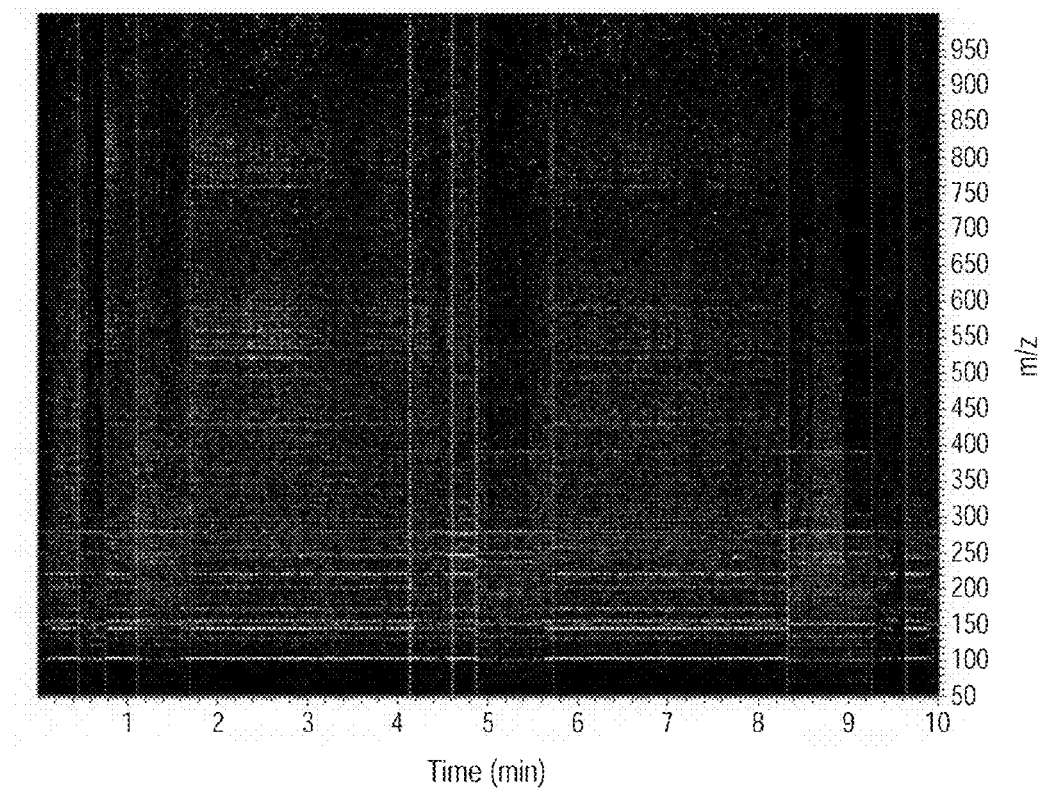
FIG. 8B is a chart illustrating a temporal change in ion intensity when the probe scans the tissue section, according to Example 2.

Next, described is a temporal change in ion intensity when the probe scans the tissue section. FIG. 8A illustrates an enlarged optical microscope image of the sample illustrated in FIG. 6, and FIG. 8B illustrates the ion intensity obtained by scanning a dotted line portion in FIG. 8A. In FIG. 8B, the horizontal axis represents time, the vertical axis represents the mass-to-charge ratio, and the amount of ions is represented by brightness contrast. Because the probe scans the sample in FIG. 8A with the passage of time, in FIG. 8B, the horizontal axis corresponds to the generation place of ions on the sample, and a whiter portion means a larger amount of ions. The above-mentioned results show that the ions in Table 1 were generated in portions on the substrate in which the sample existed. Consequently, it is confirmed that, according to the method of the present invention, components of a solid sample can be soft-ionized under an atmosphere pressure and one-dimensional distribution thereof can be captured. In order to further obtain two-dimensional distribution of the components on the sample surface, a plurality of pieces of one-dimensional distribution information may be acquired according to the method of the present invention and then may be integrated with each other.

(Mass-to-Charge Ratio: 1,000 to 2,000)

Figure 9A:
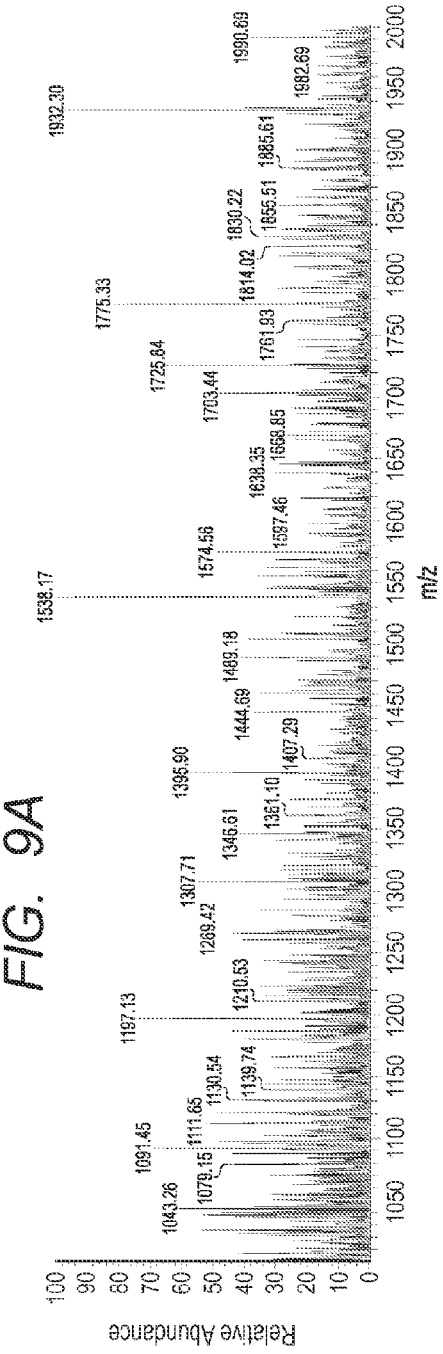
FIG. 9A illustrates a mass spectrum at a mass-to-charge ratio of 1,000 to 2,000, which is obtained in Example 2.
Figure 9B:
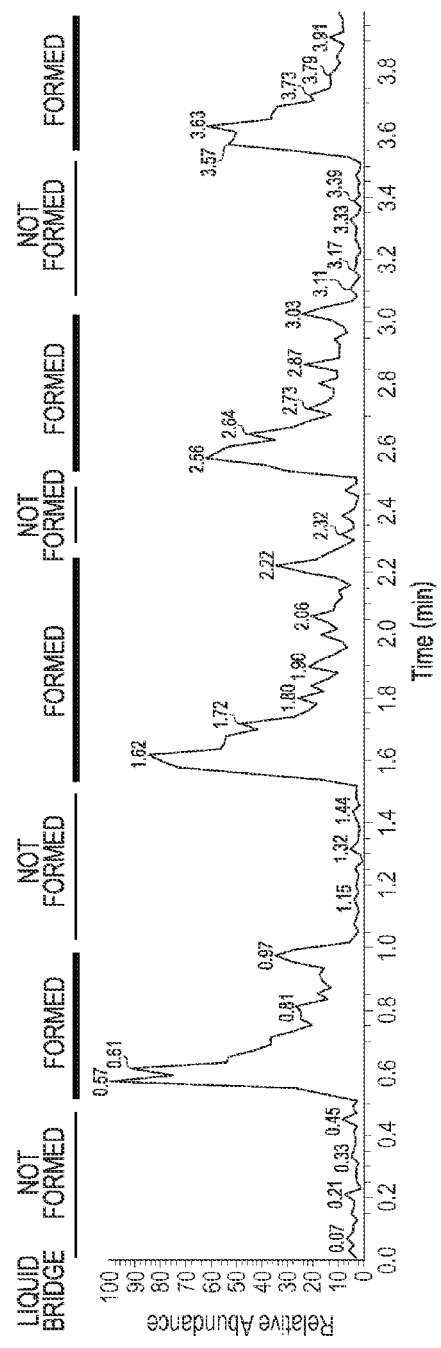
FIG. 9B illustrates a mass spectrum at a mass-to-charge ratio of 1,000 to 2,000, which is obtained in Example 2.

FIGS. 9A and 9B each illustrate the mass spectrum when the mass-to-charge ratio obtained according to the method of the present invention is 1,000 to 2,000. The sample was a pancreas tissue section of a mouse. Here, in the state where the probe was oscillated such that the sample and the leading end of the probe intermittently came closer to each other, the measurement was performed while whether or not a liquid bridge was formed was checked. That is, without scanning of the sample, in each of the state where the liquid bridge was intermittently held and the state where the probe and the sample were spaced apart from each other and where the liquid bridge disappeared, the repetition of formation and disappearance of the liquid bridge was checked, and a temporal change in mass spectrum was measured. FIGS. 9A and 9B each illustrate an experiment result obtained by continuously measuring each of the states four times. FIG. 9A illustrates the mass spectrum, and FIG. 9B illustrates a temporal change in ion intensity. Referring to FIG. 9A, the generation of a plurality of ions was observed in a range of a mass-to-charge ratio of 1,000 to 2,000. Then, the result of FIG. 9B shows that the generation and disappearance of these ions were associated with whether or not the liquid bridge was formed. This proves that, owing to the formation of the liquid bridge, components on the sample surface were dissolved in the liquid bridge and then were ionized. Note that the reason why the ion intensity decreased with the passage of time in the state where the liquid bridge was formed is considered to be as follows: in the case where the formation of the liquid bridge and ionization alternately occurred at the same place, the components on the sample surface were sequentially ionized, and the intensity of the components on the sample surface decreased. Further, according to the method described here, it is considered that an appropriate measurement time can be determined.

REFERENCE SIGNS LIST

1 probe
2 oscillation provider
3 substrate
4 liquid bridge
5 Taylor cone
6 charged micro droplets
7 ion take-in part 8 sample stage
9 liquid supplier
10 voltage applier
11 electrically conductive flow path
12 voltage applier
13 sample stage controller
14 voltage applier
15 mass spectrometer While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-045920, filed on Mar. 1, 2012, which is hereby incorporated by reference herein in its entirety.

What is claimed is:

1. An ionization method for a substance comprising steps of:
   (i) supplying a liquid onto a substrate from a probe such that a liquid comprising the substance bridge is formed with the liquid between the probe and the substrate, the probe having an end in-line with a longitudinal axis of the probe;
   (ii) oscillating the end of the probe in a direction that intersects with the longitudinal axis of the probe; and
   (iii) generating an electric field between an electrically conductive portion of the probe in contact with the liquid and an ion extraction electrode, to thereby ionize the substance contained in the liquid between the end of the probe and the ion extraction electrode.

2. The ionization method according to claim 1, wherein a position of the end of the probe in the step (i) is different from that in the step (iii).

3. The ionization method according to claim 1, wherein, in the step (iii), the liquid forms a Taylor cone at the end of the probe.

4. The ionization method according to claim 1, wherein, in the step (iii), part of the liquid escapes as charged droplets from the end of the probe.

5. The ionization method according to claim 4, wherein the charged droplets escape from a Taylor cone.

6. The ionization method according to claim 4, wherein the charged droplets cause a Rayleigh fission.

7. The ionization method according to claim 1, wherein the probe includes a plurality of flow paths.

8. The ionization method according to claim 1, wherein the probe includes a protrusion.

9. The ionization method according to claim 8, wherein the protrusion is made of a material including platinum.

10. The ionization method according to claim 1, wherein the substance is fixed onto the substrate, and the liquid dissolves the substance in a region in which the liquid bridge and the substrate come into contact with each other.

11. The ionization method according to claim 10, wherein the probe scans the substrate.

12. A mass spectrometry method comprising:
   ionizing the substance according to the ionization method according to claim 1; and
   guiding the ionized substance to a mass spectrometer, to thereby perform mass spectrometry.

13. An extraction or purification method for a substance, comprising ionizing the substance according to the ionization method according to claim 1; and separating, from the liquid, the ionized substance by means of an electric field, to thereby extract or purify the substance.

14. The ionization method according to claim 1, wherein the liquid bridge is formed between the end of the probe and the substrate in the step (i) and the liquid moves toward a side surface of the probe on a side of the ion extraction electrode to emit charged droplets of the liquid in the step (iii).

15. The ionization method according to claim 1, wherein the probe includes a plurality of flow paths configured to supply the substrate with a plurality of different liquids.

* * * * *